United States Patent [19]
Varshavsky et al.

[11] Patent Number: 5,391,490
[45] Date of Patent: Feb. 21, 1995

[54] UBIQUITIN-SPECIFIC PROTEASE

[75] Inventors: Alexander J. Varshavsky, Boston; John W. Tobias, Cambridge, both of Mass.

[73] Assignee: Massachusetts Institute of Technology, Cambridge, Mass.

[21] Appl. No.: 186,434

[22] Filed: Jan. 25, 1994

Related U.S. Application Data

[63] Continuation of Ser. No. 573,958, Aug. 28, 1990, abandoned, which is a continuation-in-part of Ser. No. 521,089, May 9, 1990, abandoned.

[51] Int. Cl.$^6$ ................................. C12N 9/60
[52] U.S. Cl. ...................... 435/224; 435/212; 435/219
[58] Field of Search ............... 530/344, 412; 435/212, 435/219, 224

[56] References Cited

FOREIGN PATENT DOCUMENTS 8802406 4/1988 WIPO.
8912678 12/1989 WIPO.

OTHER PUBLICATIONS

Nagai et al. Nature 309:810–812 (1984).
Herskho et al. PNAS 81:7021–7025 (1985).
Tsunasawa et al. J. Biol. Chem. 260:5382–5391 (1985).
Boissel et al. PNAS 82:8448–8452 (1985).
Thornton et al. J. Mol. Biol. 167:443–460 (1983).
Ferber et al. J. Biol. Chem. 261:3128–3134 (1986).
Bachmain et al. Science 234:179–186 (1986).
Ferber et al. Nature 326:808–811 (1988).
Reiss et al. J. Biol. Chem. 263:2693–2698 (1988).
Townsend et al. J. Exp. Med. 168:1211–1224 (1988).
Bachmain et al. Cell 56:1019–1032 (1989).
Chau et al. Science 243:1576–1583 (1989).
Gonda et al. J. Biol. Chem. 264:16700–16712 (1989).
Miller et al. Biotechnology 1:698–704 (1989).
Sassanfeld, Trends in Biotechnol. 8:88–93 (1990).

*Primary Examiner*—Richard A. Schwartz
*Assistant Examiner*—J. Lebuyader
*Attorney, Agent, or Firm*—Kevin M. Farrell

[57] ABSTRACT

A ubiquitin-specific protease which cleaves ubiquitin from any protein or peptide to which ubiquitin is joined and the gene encoding the protease are disclosed. The protease specifically cleaves the peptide bond in a fusion of ubiquitin to a protein or peptide between the carboxyl-terminal amino acid residue of a ubiquitin moiety and the α-amino group of any non-ubiquitin protein or peptide to which ubiquitin is joined. Recombinant expression vectors containing a DNA sequence encoding the ubiquitin-specific protease can be used to transform cells for production of the protease or to provide the cell with the ability to proteolytically deubiquitinate, in vivo, ubiquitin fusions co-produced by the cell. The protease can also be isolated and used to deubiquitinate ubiquitin fusions in vitro. For those proteins or peptides whose functional activity is inhibited or otherwise modified by the presence of a ubiquitin moiety, this moiety can be used as a temporary inhibitor (or modifier) of the activity of a protein or peptide, with the ubiquitin-specific protease employed to restore, by deubiquitination, the original activity of the protein or peptide.

7 Claims, 11 Drawing Sheets

```
  1 ttgtgatctgcgtcctttttctcaggaaaaaaatttatagacattcaagaatag
 61 aagcgattgtcaaaattcgcttcctcctttcttccattataacgtctgatcattttacg
121 tcttcagtgccctccctgttcgaactagatacttttcgaacacttctcccctttaatc 181 tacaaaatttgtatggatttgtttattgaaagcaagataaacagtttattacaattttt
                    M  D  L  F  I  E  S  K  I  N  S  L  L  Q  F  L 241 atttggttcccgacaggattttgagaaatttaaaacttggagtaacaacaataacaa
     F  G  S  R  Q  D  F  L  R  N  F  K  T  W  S  N  N  N  N  N 301 tctatcgattattatttttggcatagtagtagtgaatgacaacaacttcagaataataatag
     L  S  I  Y  L  L  I  F  G  I  V  V  F  F  Y  K  K  P  D  H 361 tctaaactacacattgttgagagcgttagtgaatgacaacaacttcagaataataatag
     L  N  Y  I  V  E  S  V  S  E  M  T  T  N  F  R  N  N  N  S 421 ccttagccgttggttgcccagaagtaagtttaccccacttagacgaagagatcttgaaaag
     L  S  R  W  L  P  R  S  K  F  T  H  L  D  E  E  I  L  K  R 481 aggtggtttcattgctggtttagttaatgatggtaacacttgttttatgaactctgtttt
     G  G  F  I  A  G  L  V  N  D  G  N  T  C  F  M  N  S  V  L
```

*FIG. 4A*

```
541  gcaatcattggcatcatccagagaattaatggagttcttggacaataatgtcataaggac
     Q  S  L  A  S  S  R  E  L  M  E  F  L  D  N  N  V  I  R  T 601  ctatgaggagatagaacaaatgaacacaatgaagaagaacgggcaagaatctgctca
     Y  E  E  I  E  Q  N  E  H  N  E  E  G  N  G  Q  E  S  A  Q 661  agatgaagccactcataagaaaaacactcgtaagggtggcaaagtttatggtaagcataa
     D  E  A  T  H  K  K  N  T  R  K  G  G  K  V  Y  G  K  H  K 721  gaagaaattgaataggaagtcaagttcgaagaagacgaagaaagagccaggagccaga
     K  K  L  N  R  K  S  S  K  E  D  E  E  K  S  Q  E  P  D 781  tataccttcagtgtcgcctaagggatctactttctgccttaaatgcaaagtattatcg
     I  P  F  S  V  A  L  R  D  L  L  S  A  L  N  A  K  Y  Y  R 841  ggataaaccctatttcaaaaccaatagtttattgaaagcaatgtccaatctccaagaaa
     D  K  P  Y  F  K  T  N  S  L  L  K  A  M  S  K  S  P  R  K 901  aaatattcttcttggctacgaccaagaggacgcgcaagaattcttccagaacatactagc
     N  I  L  L  G  Y  D  Q  E  D  A  Q  E  F  F  Q  N  I  L  A 961  cgagttggaaagtaacgttaaatcattgaatactgaaaactagaaactagaacactccagttgc
     E  L  E  S  N  V  K  S  L  N  T  E  K  L  D  T  T  P  V  A
```

FIG. 4B

```
1021  gaaatcagaattacccgatgatgctttagtaggtcaacttaacctggtgaagttggcac
       K   E   L   P   D   D   A   L   V   G   Q   L   N   L   G   E   V   G   T 1081  tgtttacattccaactgaacagattgatcctactctatactacatgacaagtccattca
       V   Y   I   P   T   E   Q   I   D   P   N   S   I   L   H   D   K   S   I   Q 1141  aaatttcacacctttcaactaatgactccttagatggtatcacggcagaaagaattgg
       N   F   T   P   F   K   L   M   T   P   L   D   G   I   T   A   E   R   I   G 1201  ttgtttacagtgtgtgagaacggtggcataagatattccgtatttcggattaagctt
       C   L   Q   C   G   E   N   G   G   I   R   Y   S   V   F   S   G   L   S   L 1261  aaatttaccgaacgagaatattggttccactttaaaattatctcagttattaagcgactg
       N   L   P   N   E   N   I   G   S   T   L   K   L   S   Q   L   L   S   D   W 1321  gagtaaacctgaaatcatcgaaggcgtagaatgtaaccgttgtgccctcacagcagcgca
       S   K   P   E   I   I   E   G   V   E   C   N   R   C   A   L   T   A   A   H 1381  ctctcatttattggtcagttgaaagaatttgaaaaaaacctgagggttcgatcccaga
       S   H   L   F   G   Q   L   K   E   F   E   K   K   P   E   G   S   I   P   E 1441  aaagccaattaacgctgtaaagataggtccatcaaatcgaagaagttcttgccaaacc
       K   P   I   N   A   V   K   D   R   V   H   Q   I   E   E   V   L   A   K   P
```

FIG. 4C

```
1501  agttattgacgatgaagagattataagagagttgcatacagcaaatatggtacgtaatgctc
          V  I  D  D  E  D  Y  K  K  L  H  T  A  N  M  V  R  K  C  S 1561  taaatctaagcagatttttaatcaagacctccaccattattccattcattcatcaacag
          K  S  K  Q  I  L  I  S  R  P  P  P  L  L  S  I  H  H  N  R 1621  atccgtatttgatccaagaacgtacatgattagaaaaataactcgaaagtattgtttaa
          S  V  F  D  P  R  T  Y  M  I  R  K  N  N  S  K  V  L  F  K 1681  gtcaaggttgaatcttgccccatggttgtgatattaatgaatcaatttggatgctcg
          S  R  L  N  L  A  P  W  C  C  D  I  N  E  I  N  L  D  A  R 1741  tttgccaatgtcaaaaaggaaaaactggcgcaacagattcaagtgaagatgaaaacat
          L  P  M  S  K  K  E  K  L  A  Q  Q  D  S  S  E  D  E  N  I 1801  tggcgggtgaatactacgaattacatgaacgcttcgagcaggatttgaagacagcga
          G  G  E  Y  Y  T  K  L  H  E  R  F  F  E  Q  I  F  E  D  S  E 1861  ggaagaaaagaatacgatgacgcagaggggaacatgcgtctcattacaatcataccaag
          E  E  K  E  Y  D  D  A  E  G  N  M  R  L  I  T  I  P  R 1921  ggatatcagtaactatgatccctaaacggtgaagtcgatggcgtgacatcgatgatga
          D  I  S  N  Y  D  P  L  N  G  E  V  D  G  V  T  S  D  D  E
```

FIG. 4D

```
1981  agatgagtacattgaagaaacegatgctttagggaatacaatcaaaaaggatcataga
       D  E  Y  I  E  E  T  D  A  L  G  N  T  I  K  K  R  I  I  E 2041  acattctgatgttgaaaacgagaatgtaaaagatgaagaactgcaagaatcgacaa
       H  S  D  V  E  N  E  N  V  K  D  N  E  E  L  Q  E  I  D  N 2101  tgtgagccttgacgaccaaagatcaactagaacatcatctgatga
       V  S  L  D  E  P  K  I  N  V  E  D  Q  L  E  T  S  S  D  E 2161  ggaagatgttataccagctccacctatcaattatgctagtcattttccacagttccagc
       E  D  V  I  P  A  P  P  I  N  Y  A  R  S  F  S  T  V  P  A 2221  cactccattgacatattcattgcgctctgtcattgttcactacggtacccatattatgg
       T  P  L  T  Y  S  L  R  S  V  I  V  H  Y  G  T  H  N  T  G 2281  tcattacattgcatttagaaaatacagggtttgttggtggagaatatctgatgagactgt
       H  Y  I  A  F  R  K  Y  R  G  C  W  R  I  S  D  E  T  V 2341  gtacgttgtggacgaagctgaagtccttcaacacccggtgtatttatgttattttacga
       Y  V  V  D  E  A  E  V  L  S  T  P  G  V  F  M  L  F  Y  E 2401  atatgactttgatgaagaactgggaagatgaaggatgaaaatgaaggattttgaagtaa
       Y  D  F  D  E  E  T  G  K  M  K  D  D  L  E  A  I  Q  S  N
```

FIG. 4E

```
2461  taatgaagaagatgatgaaaaagagagcaggagccaaaggagtccaggagccaaggaaag
       N  E  E  D  D  E  K  E  E  Q  K  G  V  Q  E  P  K  E  S
2521  ccaagagcaaggagagaaggtgaagagcaagagcagatgaagttcgagag
       Q  E  Q  E  E  G  Q  E  Q  M  K  F  E  R
2581  aacagagaccatagagatatttctggtaaagatgtaaactaagttataaatacgatatc
       T  E  D  H  R  D  I  S  G  K  D  V  N  *
2641  cgtaattgtgtaaataacaataactataattgaataattaaagtctacgttatt
2701  cgttaaatcaattgttagctagtgtacgaatgtctaaagttttgtaggacaattgcaaa
2761  aatcacttccattattatacaaatccttctaagcttcatttttcttaccattgtacttct
2821  tcaacttttctcttctcctctctcc
```

UBIQUITIN-SPECIFIC PROTEASE

GOVERNMENT SUPPORT

This work was supported by the following grants from the National Institutes of Health: GM31530 and DK39520.

RELATED APPLICATION

This application is a continuation of application Ser. No. 07/573,958, filed Aug. 28, 1990, now abandoned.

Which is a continuation-in-part application of U.S. Ser. No. 07/521,089, filed May 9, 1990, now abandoned, the contents of which are hereby incorporated by reference.

BACKGROUND

Ubiquitin (Ub) is a small polypeptide of approximately 8,500 daltons which was originally isolated from calf thymus. Early studies of ubiquitin indicated that this 76-residue protein is present in all eukaryotic cells, and that its amino acid sequence is conserved to an extent unparalleled among known proteins (for a review see Finley and Varshavsky, Trends Biochem. Sci. 10:343 (1985)). While these observations clearly suggested that ubiquitin mediates a basic cellular function, the identity of this function remained obscure until relatively recently.

The first clue emerged in 1977 when ubiquitin was found to be a part of an unusual, branched protein species, in which the carboxyl-terminal glycine of ubiquitin was joined via an isopeptide bond to the $\epsilon$-amino group of the internal lysine 119 in histone H2A (Hunt, L. T. and M. O. Dayhoff, Biochem. Biophys. Res. Comm. 74:650–655 (1977)). This type of conjugate has become known as a branched ubiquitin conjugate.

Figure 1:
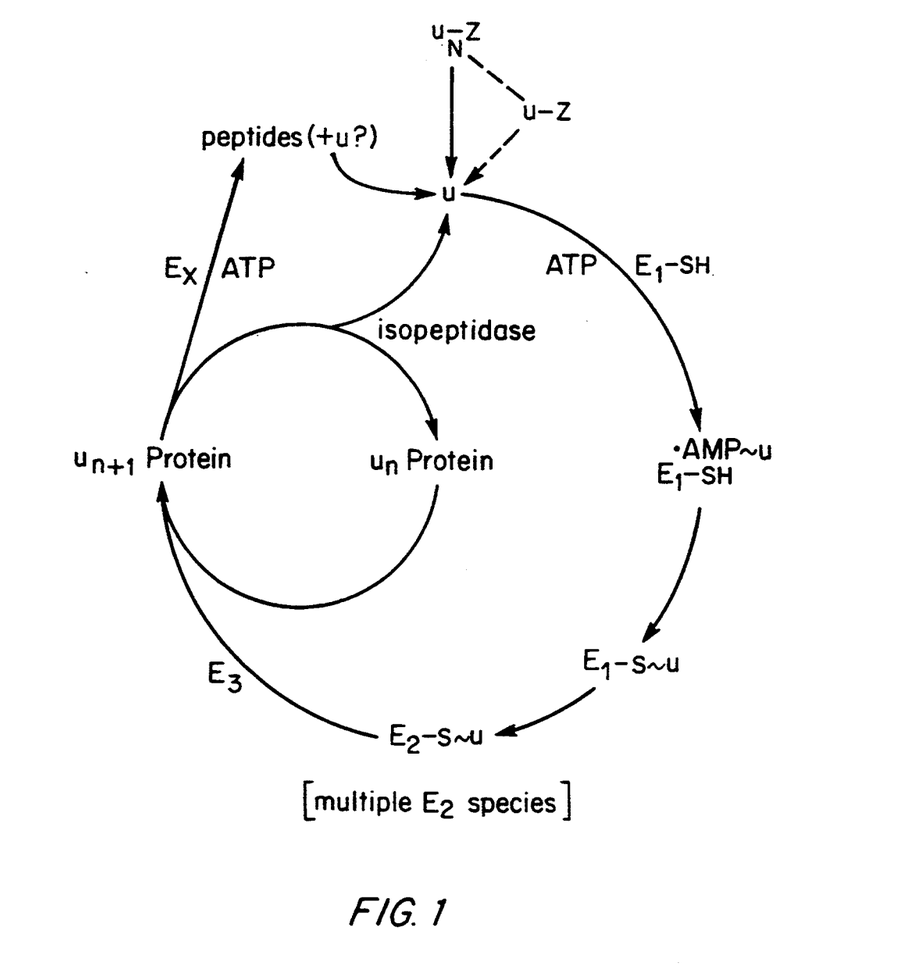
FIG. 1 shows pathways of the ubiquitin system.

Later biochemical and genetic studies indicated that one function of ubiquitin is to serve as a signal for protein degradation. Specifically, selective protein degradation was shown to require a preliminary, ATP-dependent step of ubiquitin conjugation to a targeted proteolytic substrate. The coupling of ubiquitin to other proteins is catalyzed by a family of ubiquitin-conjugating enzymes, which form an isopeptide bond between the carboxyl-terminal glycine of ubiquitin and the $\epsilon$-amino group of a lysine residue in an acceptor protein (see FIG. 1). In a multiubiquitin chain, ubiquitin itself serves as an acceptor, with several ubiquitin moieties attached sequentially to an initial acceptor protein to form a chain of branched ubiquitin-ubiquitin conjugates. Formation of the multiubiquitin chain on a targeted protein has been shown to be essential for the protein's subsequent degradation (Chau et al., Science 24:1576–1583 (1989)).

A second, non-branched type of ubiquitin-protein conjugate contains ubiquitin whose carboxyl-terminal glycine residue is joined, via a peptide bond, to the $\alpha$-amino group at the amino terminus of an acceptor protein. The resulting conjugate is a linear fusion between ubiquitin and a "downstream" protein. Although no enzymes have been found that can generate such linear ubiquitin-protein fusions posttranslationally, these ubiquitin fusions, unlike the branched ubiquitin conjugates, can be encoded by appropriately constructed DNA molecules and synthesized on ribosomes as direct products of mRNA translation.

Such DNA constructs were made and the proteins encoded by them were synthesized in vivo by Bachmair et al. (Science 234:179–186 (1986)). In particular, a chimeric gene encoding a ubiquitin-$\beta$-galactosidase (Ub-$\beta$gal) fusion protein was expressed in the yeast Saccharomyces cerevisiae. It was observed that the ubiquitin moiety of this fusion was efficiently and precisely cleaved off in vivo at the ubiquitin-$\beta$gal junction, yielding free ubiquitin and the $\beta$gal protein with its (natural) methionine residue at the amino terminus. Using site-directed mutagenesis, the authors replaced the methionine codon of $\beta$gal at the Ub-$\beta$gal junction with codons specifying each of the other 19 amino acids. The corresponding Ub-X-$\beta$gal proteins (with X denoting the junctional amino acid residue of $\beta$gal) were expressed in yeast, and the structure and metabolic fate of the products were examined. It was found that, in all cases, the ubiquitin moiety was cleaved off the Ub-X-$\beta$gal fusion protein in vivo by a ubiquitin-specific (Ub-specific) protease irrespective of the nature of the residue X at the Ub-$\beta$gal junction (when X was proline, the deubiquitination, while still occurring, was about an order of magnitude slower than with the other 19 junctional residues) (Bachmair et al., Science 234:179–186 (1986); Bachmair and Varshavsky, Cell 56:1019–1032 (1989); Gonda et al., J. Biol. Chem. 264:16700–16712 (1989)).

The resulting technique, the ubiquitin fusion methodology, has provided, among other things, a definitive solution to the so-called "methionine problem". This fundamental problem stems from the fact that, because of constraints imposed by the genetic code, all newly synthesized proteins in all organisms start with methionine. The rules that govern subsequent fate of the amino-terminal region of a newly made protein (e.g., whether the methionine will be retained, acetylated, otherwise modified or removed, or whether more extensive changes at the amino terminus would occur) are poorly understood, and therefore cannot be used to produce in vivo a specific protein or polypeptide bearing any desired (predetermined) amino-terminal residue. This poses severe problems in many biotechnological applications, for instance, when medically important eukaryotic proteins are produced by recombinant DNA methods in heterologous hosts such as yeast or bacteria. Many such proteins, when produced under normal conditions in their natural in vivo environments, bear mature amino-terminal residues that are different from those that these proteins bear when overexpressed in heterologous in vivo systems such as yeast or bacterial cells. Possession of a correct (natural) amino-terminal residue assumes particular importance in the case of recombinant proteins produced for pharmaceutical applications. For instance, incorrect (or extra) amino-terminal residues in an intravenously administered protein may present antigenicity problems (induction of immune response to a protein), or result in too rapid clearance of the protein from the bloodstream. Among the important clinical and veterinary protein drugs which fall into these groups are growth hormones, various interferons, fibroblast growth factors, and interleukins.

The invention of the ubiquitin fusion methodology has provided a definitive, generally applicable, solution to the problem of producing any desired (predetermined) amino acid residue of the amino terminus of either a protein, polypeptide or peptide (these three terms are often used interchangeably in the art, with "peptides" usually, but not always, referring to relatively short polypeptides, on the order of ~50 residues or less).

The ability to generate any desired residue at the amino terminus of a given protein, in addition to being crucial for solving the above problems, is also useful in a variety of other applications, from fashioning different amino termini of proteins or peptides for their functional studies to manipulating the metabolic stability (in vivo half-lives) of proteins by changing their amino-terminal residues (Bachmair et al., *Science* 34:179–186 (1986)).

While the facile in vivo generation of desired amino-terminal residues in specific proteins has been achieved for the first time through the ubiquitin fusion methodology, the analogous manipulation of proteins' amino termini in vitro (in cell-free systems) has previously been possible, to a limited degree, using a variety of specific proteases, such as renin or Factor Xa (Nagai and Thogersen, *Meth. Enzymol.* 153:461–466 (1987)). Unfortunately, all of these in vitro-used proteases have severe drawbacks as reagents for generating the desired amino termini in specific proteins or peptides, either because, like renin, they are not specific enough and often cleave the target protein at inappropriate places as well, or because, like Factor Xa, they are relatively inefficient, requiring long reaction times and producing low yields of the desired product.

For these reasons, from the time of the invention of the ubiquitin fusion methodology in 1986, it has always been desirable to isolate a gene for the highly efficient, exquisitely Ub-specific protease that underlied the in vivo version of the methodology and to use this protease in vitro as an alternative to the flawed proteolytic reagents that have previously been used for the in vitro manipulation of proteins' amino termini.

The isolation of a gene encoding a yeast Ub-specific protease, YUH1, and its (heterologous) expression in *E. coli* has been reported by Miller et al. (*Biotechnology* 1:698–704 (1989)). However, a closer analysis of the protease isolated by the above group has shown that it cleaves only sufficiently short ubiquitin fusion proteins, and does not cleave those fusions having a non-ubiquitin portion exceeding ~60 residues in length. In particular, as Miller et al. stated in their abovecited paper, the YUH1 protease is incapable of deubiquitinating Ub-X-βgal proteins, the very ubiquitin fusions that have been used to establish the in vivo version of the ubiquitin fusion methodology by Bachmair et al., *Science* 234:179–186 (1986). (The X-βgal moiety of Ub-X-βgal is ~1,000 residues long.)

SUMMARY OF THE INVENTION

This invention pertains to a new type of Ub-specific protease (designated Ubiquitin-Protease 1 (UBP1)) and to isolated nucleic acid encoding UBP1 protease. The UBP1 protease deubiquitinates any fusion protein between ubiquitin and a protein or peptide other than ubiquitin, without limitation on the size of a non-ubiquitin component of the fusion. Thus, UBP1 has a qualitatively different substrate specificity from that of the previously isolated YUH1 protease. This invention also pertains to recombinant vectors expressing the UBP1 protease, to cells transformed with such vectors, and to specific versions of ubiquitin-protein fusions that facilitate isolation and manipulation of non-ubiquitin portions of these fusions using the UBP1 protease.

The compositions and methods of this invention facilitate large-scale production of the UBP1 protease. The availability of this new type of Ub-specific protease introduces an in vitro counterpart of the ubiquitin fusion methodology. The UBP1 protease provides for more efficient methods of isolation and purification of various recombinant proteins or peptides.

BRIEF DESCRIPTION OF THE FIGURES

FIG. 6 shows (A) a map of the expression vector pJTUP which encodes a sandwich fusion protein DHFR-Ubiquitin-Met-βgal; and (B) results of electrophoretic analysis of DHFR-ubiquitin-Met-βgal treated with the ubiquitin-specific protease UBP1.

DETAILED DESCRIPTION OF THE INVENTION

UBP1, the Ub-specific protease of this invention, specifically cleaves ubiquitin from any non-ubiquitin protein or peptide to which the ubiquitin is joined. Importantly, UBP1 cleaves any ubiquitin fusion (except polyubiquitin) without upper or lower limits on the size of the non-ubiquitin portion of a ubiquitin fusion. UBP1 cleaves at the junction between the ubiquitin and the non-ubiquitin protein or peptide; i.e., it cleaves the peptide bond in a ubiquitin fusion protein between the carboxy-terminal residue of a ubiquitin moiety and the α-amino group of any non-ubiquitin protein or peptide to which it is joined.

UBP1 also recognizes and cleaves "sandwich" ubiquitin fusions in which the ubiquitin moiety is located between a first and a second non-ubiquitin moiety. As used herein, the first non-ubiquitin moiety is a non-ubiquitin protein or peptide positioned upstream of the ubiquitin moiety in the sandwich ubiquitin fusion. The second non-ubiquitin moiety is a non-ubiquitin protein or peptide positioned downstream of the ubiquitin moiety in the sandwich fusion protein. UBP1 cleaves the sandwich fusion protein between the carboxy-terminal residue of the ubiquitin moiety and the α-amino group of the second non-ubiquitin moiety.

The first non-ubiquitin moiety in a sandwich ubiquitin fusion can be any peptide or protein. The sandwich ubiquitin fusion proteins can be generated, for example, by ligating DNA fragments encoding the first and second non-ubiquitin moieties to the 5' and 3' ends, respectively, of a DNA sequence encoding ubiquitin. These coding sequences must be joined in frame, in a context appropriate for expression, such that no stop codons are generated which would prematurely terminate the translation of the mRNA encoding the sandwich fusion. As described below in the Exemplification, a sandwich ubiquitin fusion protein (DHFR-Ub-Met-βgal), in which the ubiquitin moiety is located between a first and a second non-ubiquitin moiety, has been constructed, expressed, and shown to be cleaved efficiently and specifically by UBP1.

Such a sandwich construct is particularly useful in situations wherein the first non-ubiquitin moiety confers some desirable property on the sandwich ubiquitin fusion. For example, the first non-ubiquitin moiety may facilitate affinity purification of the ubiquitin fusion protein. In such a case, the fusion protein can be expressed in a cell (e.g., E. coli) that lacks Ub-specific proteases, and a cellular lysate can be passed over an affinity column specific for the first non-ubiquitin moiety. One example of a protein which is useful for affinity purification is streptavidin (Sassenfeld, K. M., Trends Biotech. 8:88–93 (1990)). Following affinity purification of the fusion protein, the latter is contacted with the ubiqutin-specific protease of this invention. The second non-ubiquitin moiety is thereby liberated from the sandwich ubiquitin fusion construct.

In contrast to UBP1, the previously isolated YUH1 enzyme cleaves ubiquitin off a ubiquitin fusion only if the non-ubiquitin portion of a fusion is relatively short (shorter than about 60 residues; see above). Since, for instance, many of the pharmaceutically important proteins are much longer than 60 residues, the YUH1 protease cannot be used to deubiquitinate fusions of these proteins with ubiquitin. In contrast, the UBP1 protease can be used for this purpose, thereby allowing the generation of desired residues at the amino termini of either large or small proteins, polypeptides or peptides (as explained above, these terms are often used interchangeably in the art).

A variety of recombinant DNA approaches could, in principle, be used to isolate the UBP1 gene. Typically, such an isolation procedure involves the construction of a cDNA or genomic DNA library from an organism known to produce UBP1. Any eukaryotic organism is an appropriate source of nucleic acid for the construction of recombinant libraries since ubiquitin is known to be produced in every eukaryote tested. Furthermore, ubiquitin is the most highly conserved eukaryotic protein identified to date. Protocols for the production and screening of cDNA libraries or genomic DNA libraries are well known to those skilled in the art.

The screening approach actually taken by the inventors named in this application was a particular version of the genetically based cloning strategy called sib selection. This method exploits the fact that, unlike eukaryotic organisms, bacteria such as E. coli lack the eukaryotic ubiquitin system, and in particular, Ub-specific proteases. It is this lack of Ub-specific proteases in bacteria that has been exploited to isolate a yeast (S. cerevisiae) gene encoding the desired Ub-specific protease. Sib selection is a method of sequential fractionation of DNA clones which is particularly useful in the absence of a selectable phenotype or sequence information. This method is detailed in the Exemplification section which follows.

In a preferred embodiment, the isolated DNA sequence of the invention encodes the amino acid sequence set forth in FIG. 4, or modifications of this sequence in which amino acids have been deleted, inserted or substituted without essentially detracting from the activity and substrate specificity of the encoded product. In FIG. 4, the UBP1 open reading frame starts at position 194 of the nucleotide sequence, and ends at position 2622, with a stop codon at position 2623. This reading frame encodes a protein of 809 residues, indicated by one-letter designations. This DNA can be isolated by the methods outlined above or the DNA can be made in vitro by conventional chemical DNA synthesis.

The isolated DNA of this invention can be used to express UBP1 in large quantities. For this purpose, the DNA is inserted into a prokaryotic or eukaryotic expression vector, with appropriate regulatory signals, and used to transform cells. A variety of appropriate vectors and regulatory signals have been previously developed for this purpose and are well known to those skilled in the art. UBP1 can be expressed in eukaryotic or prokaryotic cells. Previous work has indicated that prokaryotes lack both ubiquitin and Ub-specific enzymes (see, for example Finley and Varshavsky, Trends Biochem. Sci. 10:343 (1985); and Ozkaynak et al., Nature 312:663 (1984)). Large quantities of the protease can be produced and isolated from either bacterial or yeast cultures using appropriate expression vectors well known to those skilled in the art.

The Ub-specific protease can be used to cleave ubiquitin off ubiquitin fusions in vitro. The UBP1 protease is contacted with the ubiquitin fusion under conditions appropriate for proteolytic cleavage and the cleaved adduct is recovered. In this procedure, UBP1 can be used in free form or it can be immobilized on a solid phase such as a bead. As mentioned, UBP1 cleaves ubiquitin from large adducts as well as small. Thus, proteins or peptides can be produced as ubiquitin fusions in appropriate systems in vivo, and the ubiquitin moiety can be removed in vitro using the Ub-specific protease.

In addition, prokaryotic cells harboring an expression vector encoding the protease can be transformed with an expression vector encoding a ubiquitin fusion protein or peptide of interest. These cells will then produce a deubiquitinated product having a predetermined amino-terminal amino acid residue. There are many well known advantages to producing recombinant proteins in prokaryotic organisms such as E. coli.

In some fusions of ubiquitin to a non-ubiquitin protein or peptide, the presence of the ubiquitin moiety may inhibit or modify the functional activity of the non-ubiquitin protein or peptide. In this case, ubiquitin can be used as a temporary inhibitor (or modifier) of the functional activity of the non-ubiquitin protein or peptide with the ability to restore the original functional activity at any desired time, either in vitro or in vivo, by contacting the corresponding ubiquitin fusion with the Ub-specific protease to cleave the ubiquitin moiety.

The invention is further illustrated by the followed Exemplification.

EXEMPLIFICATION

EXAMPLE 1

Escherichia coli (strain HB101) transformed with a Saccharomyces cerevisiae genomic library was used for a sib selection strategy. The library, RB237, was produced by partially digesting yeast genomic DNA with SauIIIA and ligating the fragments into the BamH1 site in the Tet$^R$ gene of the yeast/E. coli shuttle vector YCp50. Upon initial analysis, the library contained inserts with an average size of ~19 Kb.

E. coli, transformed with the above library, was plated on agar containing Luria Broth (LB) and ampicillin (amp) (100 µg/ml) at a density of about 40 viable cells per plate. The plates were incubated at 36° C. for 16 hours. The colonies were then replicated onto LB/amp plates. The original plates were stored at 4° C., and their replicas were grown for 24 hours at 36° C. Each replicate was eluted with 1 ml of LB/amp (50 μg/ml) by repeated washing over the surface of the plate until all of the colonies were loosened into the liquid. The entire eluate was then added to 4 ml of LB/amp, and incubated on a roller drum at 36° C. overnight.

The E. coli cells in these overnight (stationary-phase) cultures were then lysed. 1.7 ml of each culture was placed in a microcentrifuge tube on ice, and then centrifuged at 12,000×g for 1 min at 4° C. The cell pellet was resuspended, by vortexing at high speed, in 50 μl of 25% sucrose (w/v), 250 mM Tris-HCl (pH 8.0). 10 μl of freshly made lysozyme solution (10 mg/ml chicken egg-white lysozyme (Sigma) in 0.25M Tris-HCl, pH 8.0) was then added, and mixed by light vortexing. The suspension was incubated on ice for 5 min. 150 μl of 75 mM EDTA, 0.33M Tris-HCl (pH 8.0) was added, mixed by light vortexing, and the tube was incubated on ice for 5 min, with occasional stirring. 1 μl of 10% Triton X-100 (Pierce) was then added to each tube, and mixed by pipetting. The cell lysate was centrifuged at 12,000×g for 15 min at 4° C. The supernatant was retained on ice, and the pellet was discarded.

In an assay for the Ub-specific protease activity, 9 μl of the above supernatant was combined with 1 μl of $^{35}$S-labeled ubiquitin-dihydrofolate reductase (Ub-Met-DHFR) fusion in a 0.5 ml microcentrifuge tube, and incubated at 36° C. for 3 hr. 5 μl of a 3-fold concentrated electrophoretic sample buffer (30% glycerol, 3% SDS (w/v), 15 mM EDTA, 0.2M 2-mercaptoethanol, 0.3 μg/ml bromophenol blue, 375 mM Tris-HCl, pH 6.8) was then added, and each tube was placed in a boiling water bath for 3 min. The samples were loaded onto a 12% polyacrylamide-SDS gel, and electrophoresed at 50 V until the bromophenol dye reached the bottom of the gel. Positions of the radioactively labeled proteins in the gel were visualized by fluorography. The gel was washed in 10% acetic acid, 25% methanol for 15 min, rinsed in H$_2$O for 15 min, and incubated with Autofluor (National Diagnostics) for 1 hr. The gel was then dried at 80° C. under vacuum, placed in a light-proof cassette against Kodak XAR-5 film and stored at −85° C. overnight.

$^{35}$S-labeled Ub-Met-DHFR was prepared as follows. Luria Broth (50 ml) supplemented with 50 μg/ml ampicillin was inoculated with 1 ml of a saturated overnight culture of E. coli strain JM101 containing a plasmid expressing the Ub-Met-DHFR fusion protein from an IPTG-inducible, highly active derivative of the lac promoter. The cells were grown with shaking at 37° C. until they reached an A$_{600}$ of ∼0.9. The culture was chilled on ice for 15 min, then centrifuged at 3000×g for 5 min and washed 2 times with M9 salts at 0° C. The cells were resuspended after the final wash in 25 ml M9 salts supplemented with 0.2% glucose, 1.8 μg/ml thiamine, 40 μg/ml ampicillin, 1 mM IPTG, 0.0625% (w/v) methionine assay medium (Difco). The suspension was then shaken for 1 hr at 37° C. and the cells were labeled by the addition of 1 mCi of $^{35}$S-Translabel (ICN), followed by a 5-min incubation, with shaking. Unlabeled L-methionine was then added to a final concentration of 0.0032% (w/v), and the cells were shaken for an additional 10 min. The cells were then harvested (3000×g for 5 min) and washed once in cold M9 salts. After the M9 wash, the cell pellet was resuspended in 0.5 ml 25% Sucrose, 50 mM Tris-HCl (pH 8.0), and incubated on ice for 5 min. During this time, chicken egg-white lysozyme (Sigma) was dissolved freshly in 250 mM Tris-HCl (pH 8.0) to a concentration of 10 mg/ml. 10 μl of the lysozyme solution was added to the cell suspension, mixed, and incubated for 5 min at 0° C. 5 μl of 0.5M EDTA (pH 8.0) was then added, and the suspension left at 0° C. for 5 min, with intermittent mixing. The cell suspension was then added to a centrifuge tube containing 0.975 ml of 65 mM EDTA (pH 8.0), 50 mM Tris-HCl (pH 8.0) and protease inhibitors, antipain, chymostatin, leupeptin, aprotinin and pepstatin, each at 25 μg/ml. 10 μl 10% Triton X-100 (Pierce) was then added, and dispersed by pipetting. The lysate was centrifuged at 39,000×g for 30 min. The supernatant was retained, quickly frozen in liquid nitrogen, and stored at −85° C.

To affinity-purify the $^{35}$S-labeled Ub-Met-DHFR, a methotrexate (MTX)-agarose affinity matrix was prepared according to the method of Kaufman (Kaufman, B. T., Meth. Enzymol. 34:272–281 (1974)). A 0.5 ml bed volume column was filled with the MTX-agarose, and washed with 10 ml of MTX column buffer (20 mM Hepes (pH 7.5), 1 mM EDTA 200 mM NaCl, 0.2 mM dithiothreitol. The $^{35}$S-labeled supernatant of the preceding step (see above) was thawed and applied to the MTX-agarose column. The column was washed with 50 ml of MTX column buffer, 50 ml of MTX column buffer containing 2M urea., and again with 50 ml of MTX column buffer. The labeled Ub-Met-DHFR was eluted from the column with folic acid elution buffer (0.2M potassium borate (pH 9.0), 1M KCl, 1 mM DTT, 1 mM EDTA, 10 mM folic acid). The elution buffer was applied to the column in 1 ml aliquots, and 1 ml fractions were collected. The fractions were assayed for $^{35}$S radioactivity and those fractions that contained the major radioactive peak were pooled. The pooled fractions were dialyzed for ∼20 hr against two changes of a storage buffer containing 40 mM Tris-HCl (pH 7.5), 1 mM MgCl$_2$, 0.1 mM EDTA, 50% glycerol. The purified $^{35}$S-labeled Ub-Met-DHFR was assayed by SDS-PAGE, followed by fluorography, and found to be greater than 95% pure.

Figure 2:
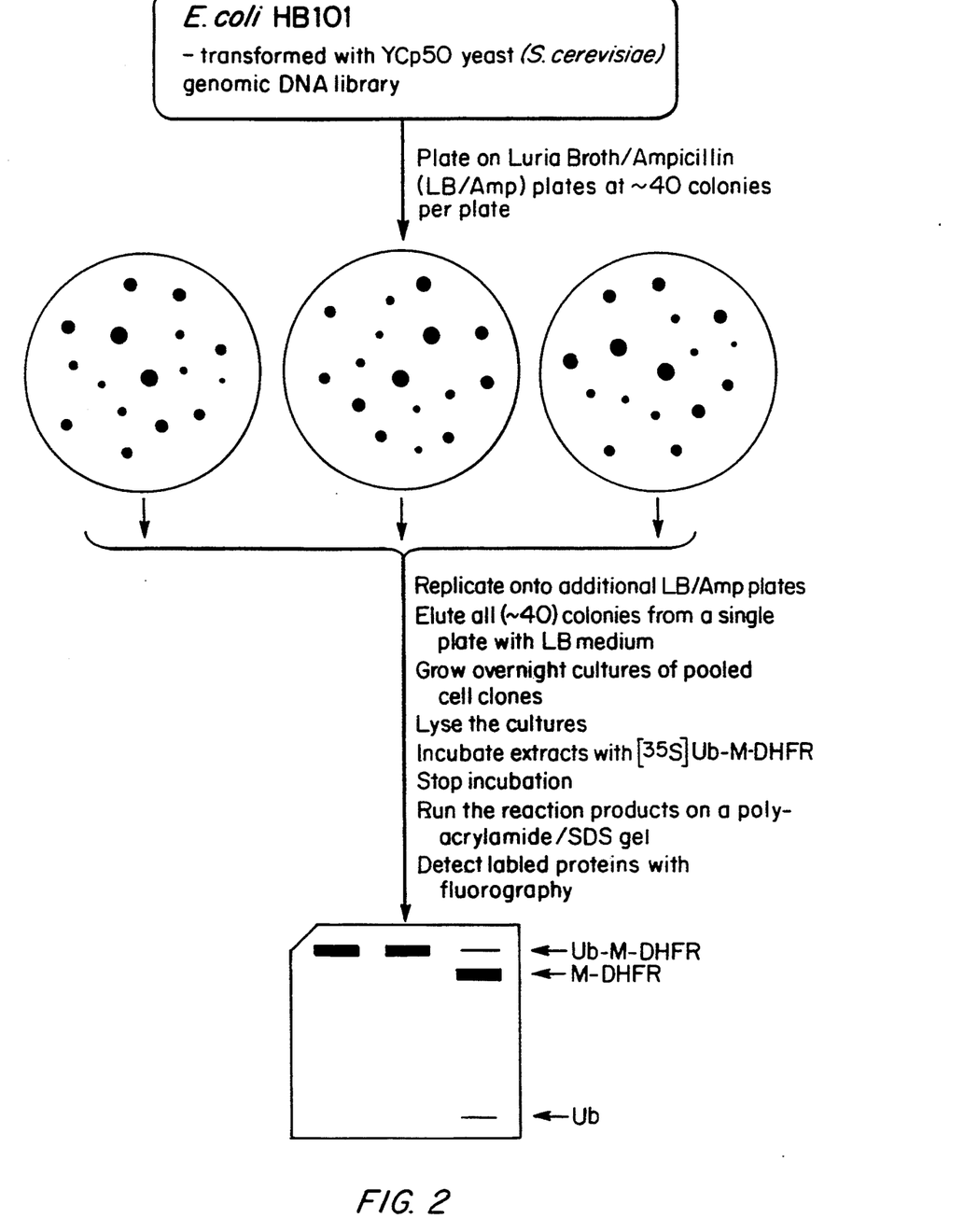
FIG. 2 shows an outline of the sib selection strategy used to isolate the yeast UBP1 gene.

The above deubiquitination assay was repeated with lysates from different pools of E. coli transformants until the gel analysis revealed a lysate that displayed proteolytic activity acting at the ubiquitin-DHFR junction (FIG. 2). This result indicated that at least one of the ∼40 E. coli colonies on the original LB/amp plate (from which the pooled lysate had been derived) contained a YCp50-based plasmid having a yeast DNA insert conferring Ub-specific proteolytic activity.

The next step of this sib selection approach to cloning the UBP1 gene was to carry out a similar Ub-Met-DHFR cleavage assay to determine which of the ∼40 colonies in a "positive" pool contained the desired plasmid. To do so, a sample of each individual colony on the plate of interest was inoculated into LB/amp and grown overnight. The Ub-Met-DHFR cleavage assay was then repeated exactly as above, but this time each lysate sample was representative of a single clonal E. coli transformant rather than a mixture of ∼40 such transformants. This analysis revealed a single colony that contained a plasmid which conferred the ability to specifically cleave at the Ub-DHFR junction, thereby accomplishing the goal of cloning a S. cerevistae gene encoding the Ub-specific protease.

Analysis of the initially isolated plasmid (pJT55) revealed a ∼15 kb insert of yeast genomic DNA in the YCp50 vector. SphI digestion of this plasmid yielded a ~14 kb fragment, which, upon subcloning into the vector pUC19, conferred the same proteolytic activity. This plasmid was called pJT57. The ~14 kb fragment was subcloned further by cutting with SphI and XhoI, isolating the ~5.5 kb fragment of the insert DNA and subcloning it into the pUC19 vector pre-cut with SphI and SalI. This resulted in the ~8.1 kb plasmid pJT60 containing the ~5.5 kb yeast DNA insert that conferred the same Ub-specific proteolytic activity as the original plasmid.

Figure 3:
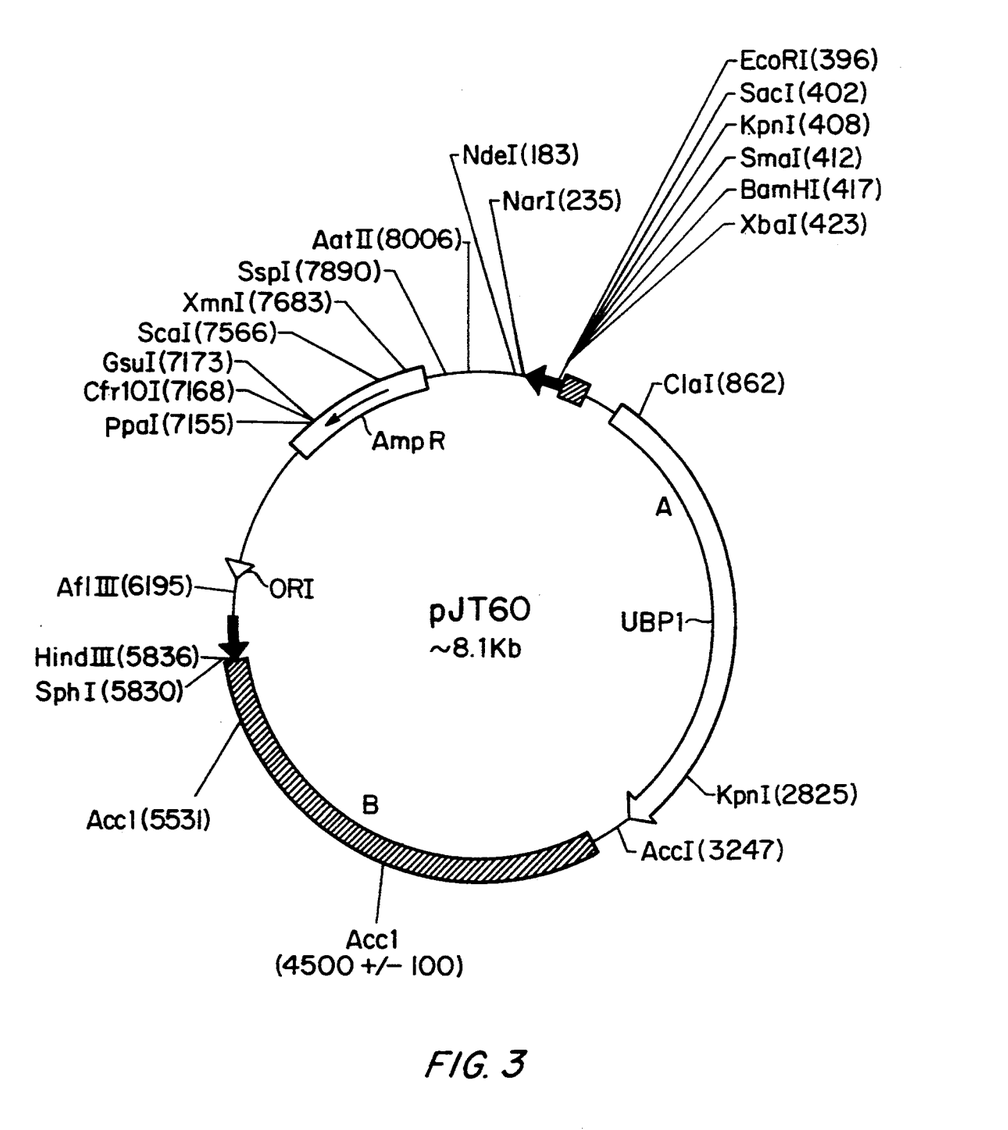
FIG. 3 shows the map of the plasmid pJT60 that encodes the UBP1 protease.
Figure 4A:
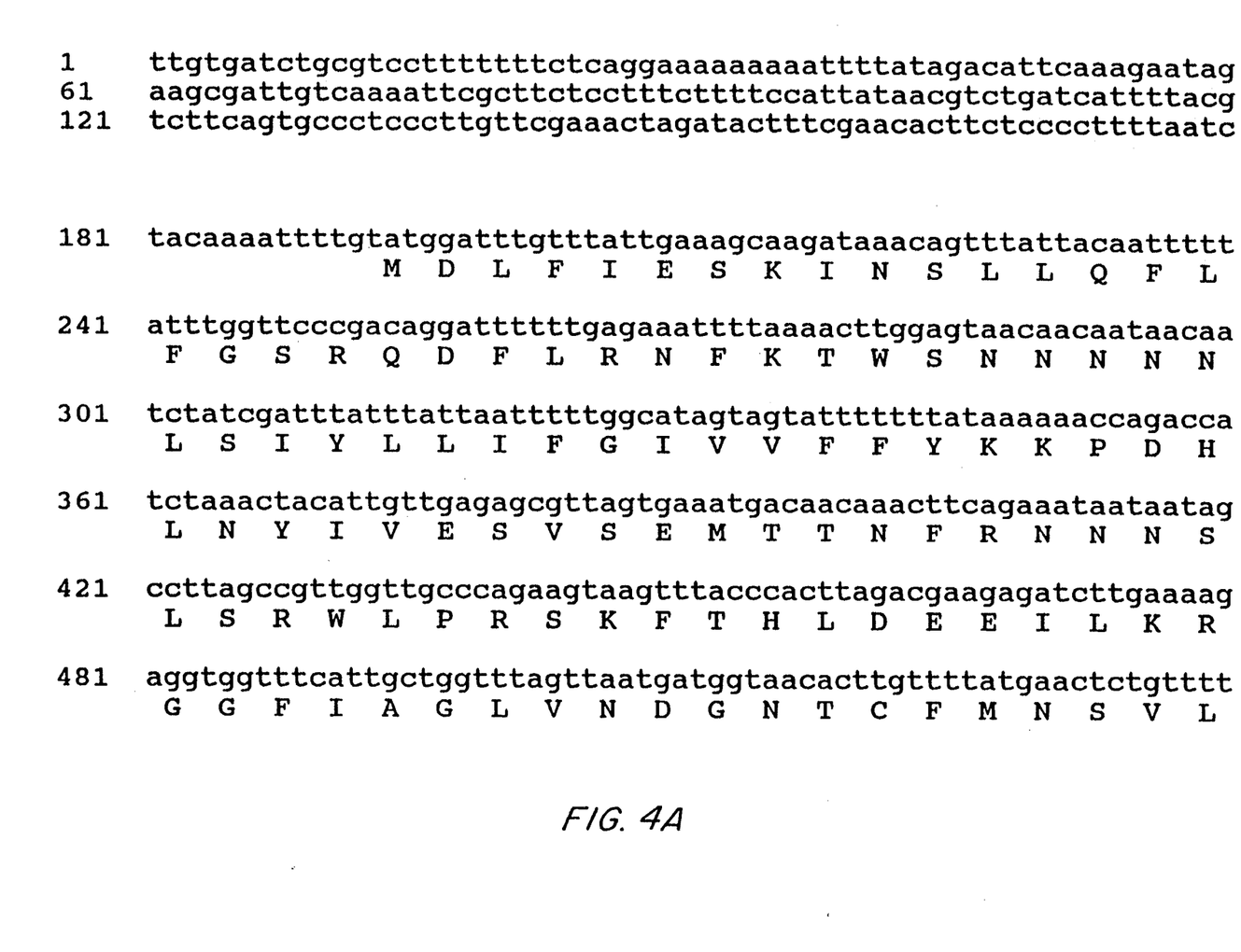
FIG. 4 shows the nucleotide sequence of the UBP1 gene and the amino acid sequence of the UBP1 protease.
Figure 4B:
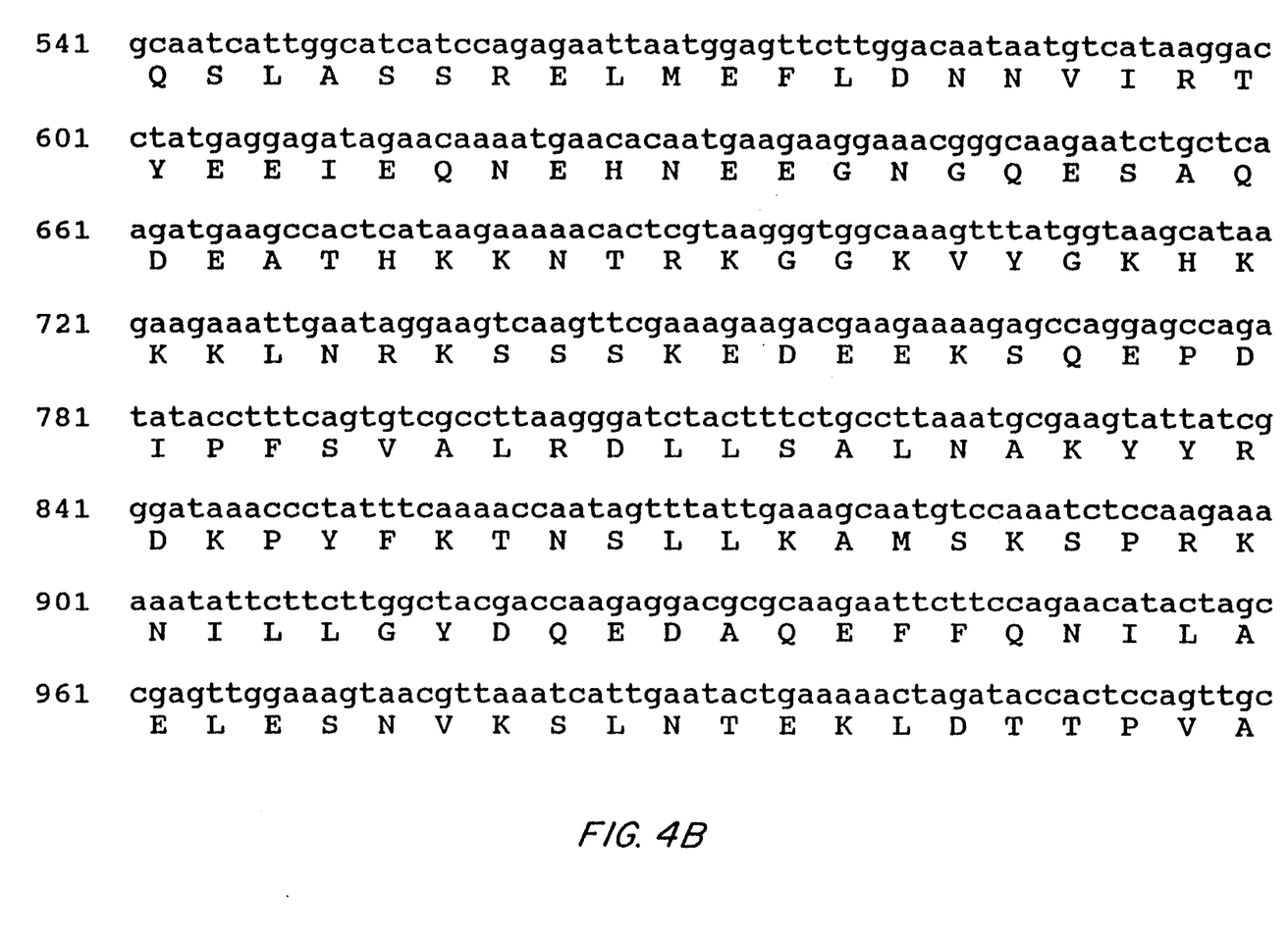
Figure 4C:
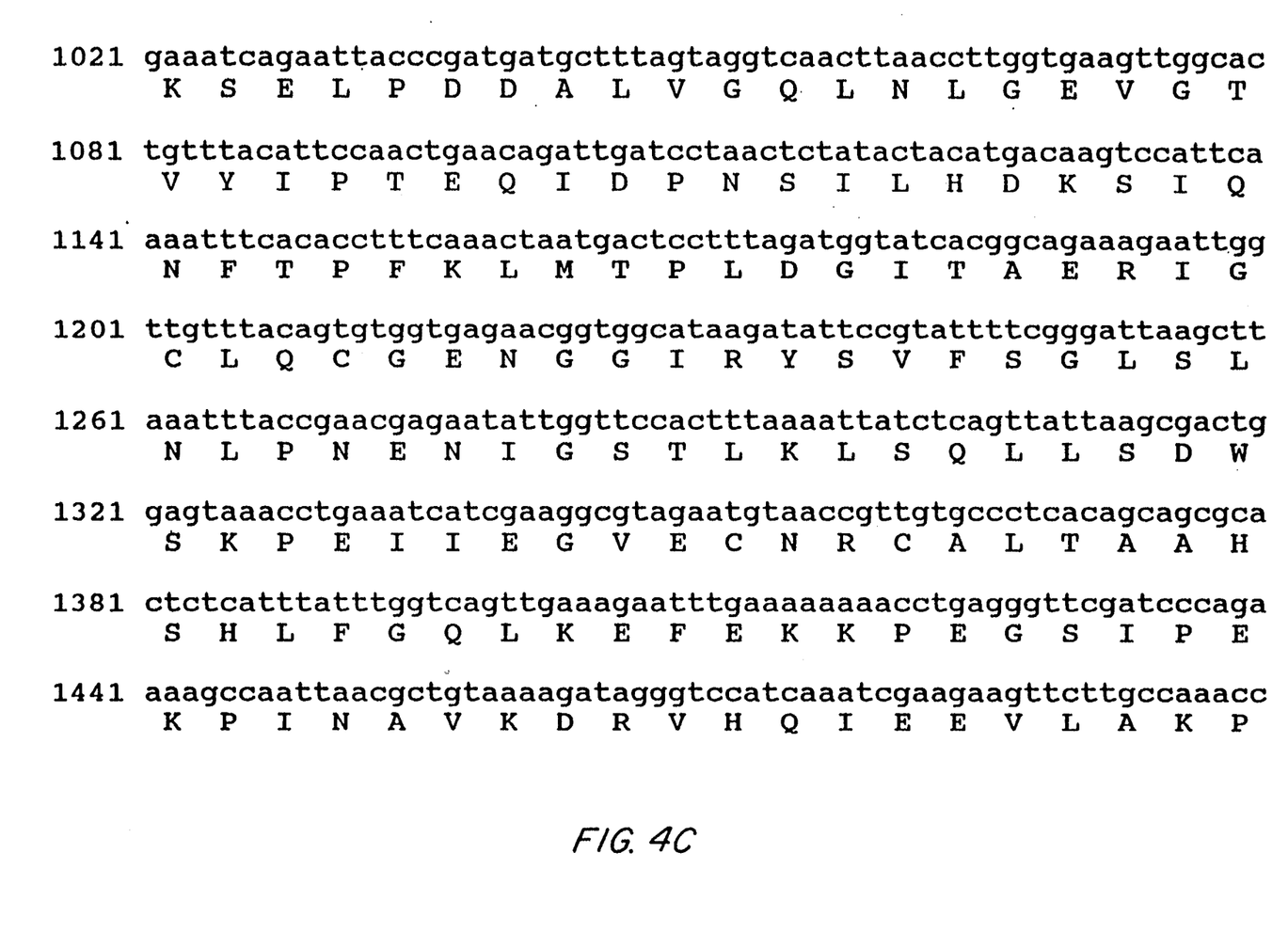
Figure 4D:
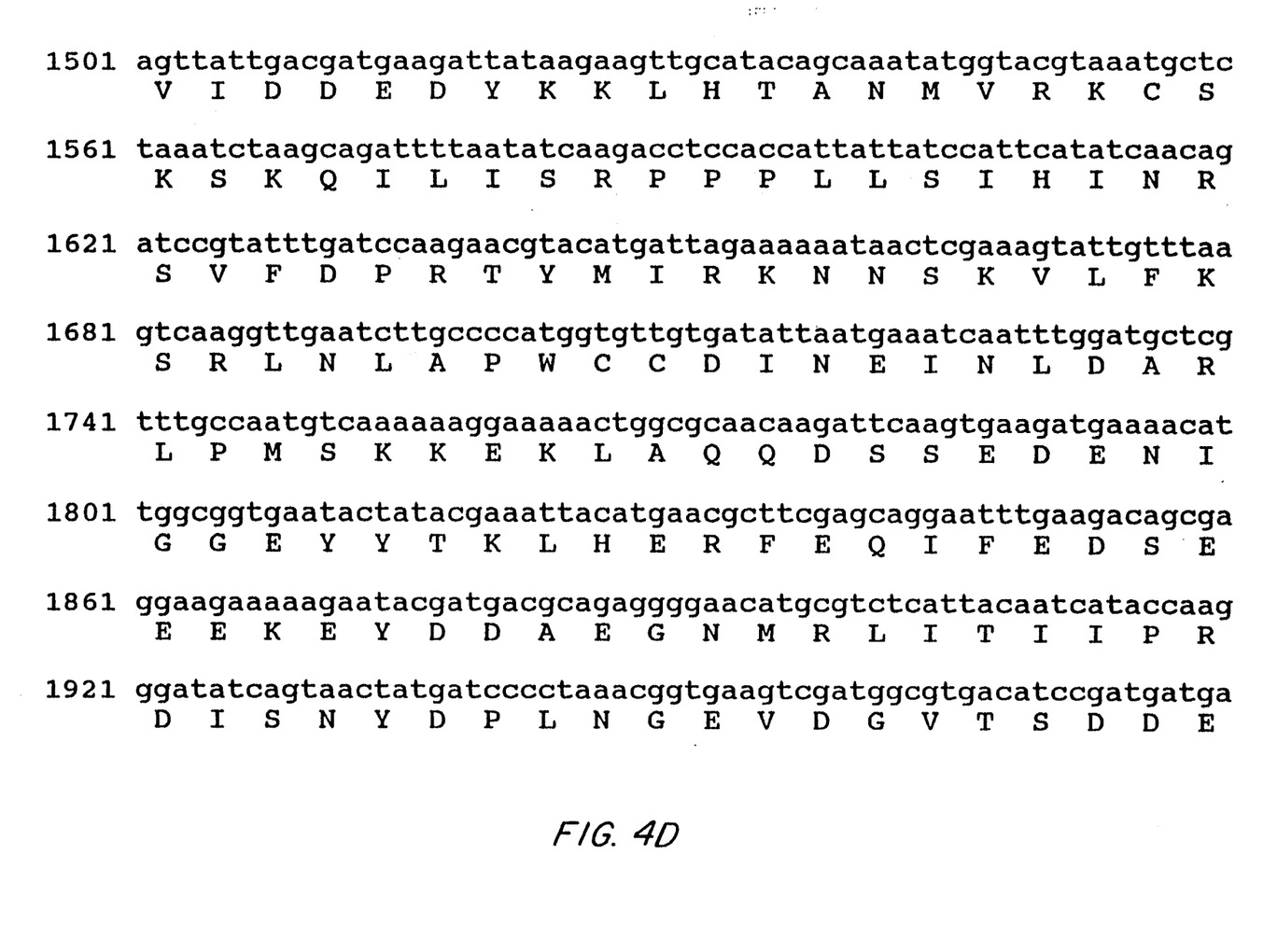
Figure 4E:
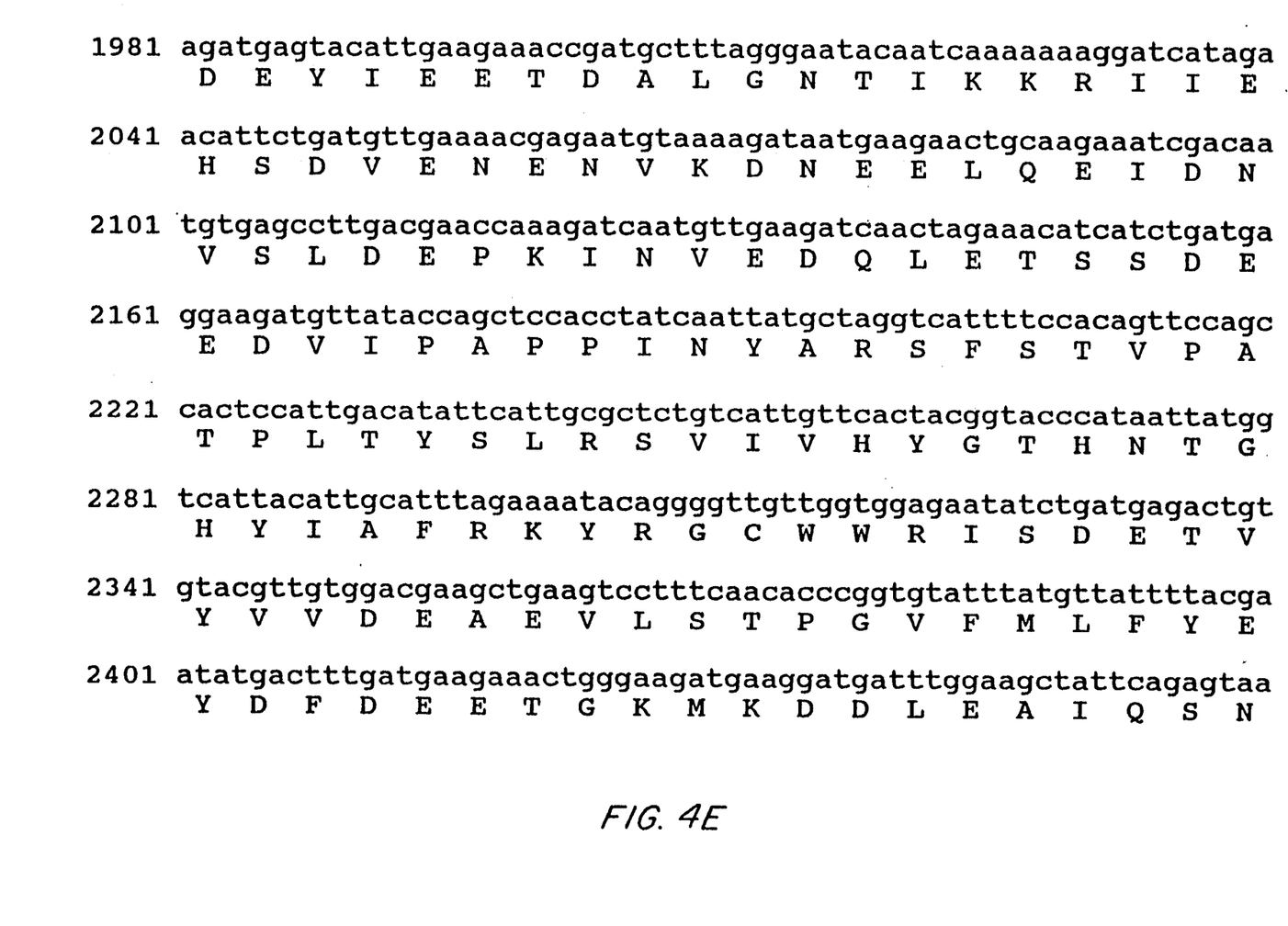
Figure 4F:
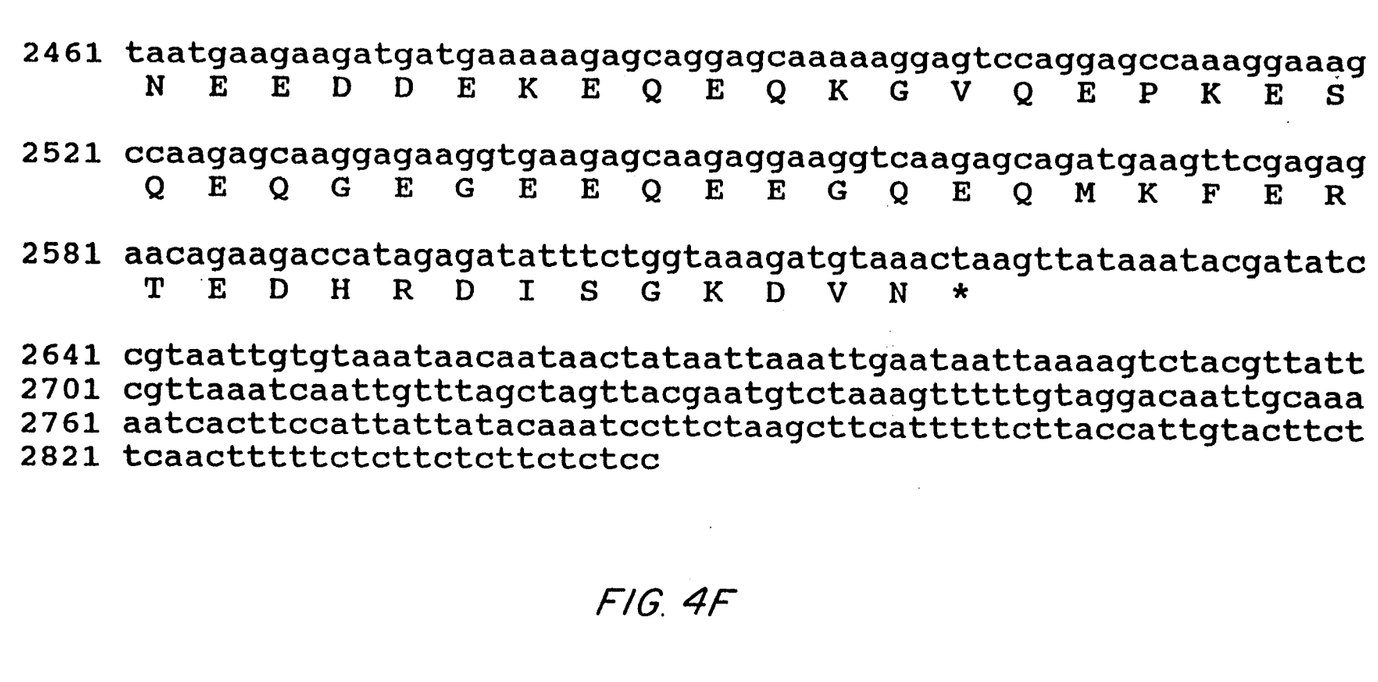

A map showing restriction endonuclease recognition sites in plasmid pJT60 is shown in FIG. 3. In the map, base pair positions are indicated by a number in parentheses following a restriction site. The yeast DNA insert in pJT60 contained a KpnI site near its center that divided the insert into two smaller fragments A and B (bases 423 to 5830). In this fragment, the open arrow indicates the open reading frame (ORF) that codes for UBP1. The entire ORF, and the thin lines bracketing it, represent the extent of the sequenced DNA shown in FIG. 4. Both fragments were subcloned into pUC19, yielding pJT60A and pJT60B. Fragment A was isolated from pJT57 after cutting with KpnI and SphI. This fragment was subcloned into pUC19 that had been cut with the same restriction endonucleases. Fragment B was isolated from pJT57 that had been cut by KpnI and XhoI; it was subcloned into pUC19 that had been cut by KpnI and SalI. Neither pJT60A nor pJT60B was able to confer Ub-specific proteolytic activity. This result suggested that the gene of interest straddled the KpnI site of the ~5.5 kb insert of pJT60.

To sequence the cloned gene, the inserts of pJT60A and pJT60B were subcloned into the M13mp19 phage vector. Nucleotide sequence was determined (using the chain termination method) in both directions from the internal KpnI site in pJT60. The KpnI site was found to be ensconced within an open reading frame extending from this site in both directions. Unidirectional deletions were then made in the sequencing templates by the methods of Dale et al. (Plasmid 13:31–40 (1989)) and the entire open reading frame (ORF) was determined (FIG. 4). The 5' end of the ORF was in fragment B and the termination codon was in fragment A. The ORF was 2427 nucleotides long, and encoded an 809-residue protein, with a molecular mass of 93 kD. The sequenced ORF was then isolated on a 2.8 kb fragment by cutting pJT60 with AccI, filling in the 5' overhangs with Klenow PolI, and ligating SalI linkers to the blunt ends. This construct was digested with SalI and BamHI, the 2.8 kb fragment was electrophoretically purified and ligated into pUC19 that had been digested with BamHI and SalI. The resulting plasmid was called pJT70. This plasmid, when transformed into *E. coli*, was able to confer the Ub-specific proteolytic activity to the same extent as either the original ~15 kb insert in YCp50 or the ~5.5 kb insert of the pJT60 plasmid that includes the ~2.8 kb fragment of pJT70. The plasmid pJT60 has been deposited with the American Type Culture Collection (Rockville, Md.), and has been assigned ATCC designation 68211. The 2.8 kb fragment contained no other ORFs of significant size, indicating that the sequenced ORF shown in FIG. 4 encoded the Ub-specific protease.

This new gene has been named UBP1, for Ubiquitin-specific protease. This designation conforms to the existing convention for naming genes associated with the ubiquitin pathway (Finley, Bartel and Varshavsky, *Nature* 338, 394–401 (1989)).

Figure 5A:
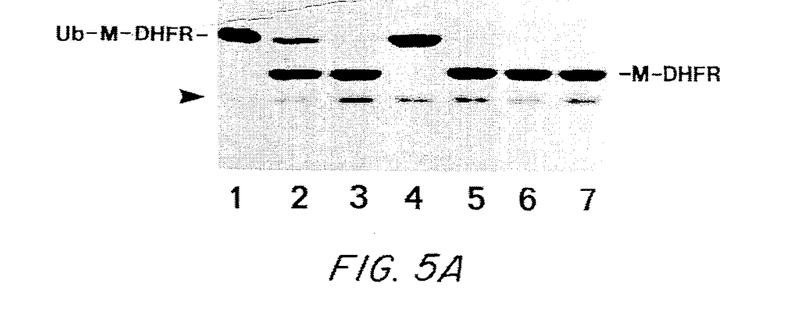
FIG. 5 shows the results of electrophoretic analysis of Ubiquitin-Met-βgal, ubiquitin-Met-DHFR and other ubiquitin fusions treated with Ub-specific protease UBP1.

The substrate specificity of the UBP1 gene product was examined, and results are shown in FIG. 5. FIG. 5A shows a fluorograph of a 12% polyacrylamide-SDS gel used to detect deubiquitinating proteolytic activity, with Ub-Met-DHFR as a substrate, and a set of subclones of a yeast DNA fragment that confers Ub-specific proteolytic activity upon *E. coli*. Each lane corresponds to a sample of the purified [$^{35}$S]Ub-Met-DHFR treated with an extract of *E. coli* and fractionated by gel electrophoresis. Lanes 1 and 4 indicate a lack of Ub-specific proteolytic activity and lanes 2,3 and 5–7 indicate the presence of such an activity. In lane 1, the substrate was treated with extract from untransformed (control) JM101 *E. coli*. In lane 2, the treatment was with the extract from JM101 containing the initial plasmid pJT55. Lanes 4–7 correspond to extracts from JM101 containing plasmids that bear different subclones (in the vector pUC19) of the initial *S. cerevisiae* genomic DNA insert present in pJT55. One plasmid that conferred the Ub-specific proteolytic activity (lane 6) was named pJT57, and was used in the construction of pJT60 (as described above). An arrowhead indicates a minor contaminant that is present in the [$^{35}$S]Ub-Met-DHFR preparation.

Figure 5B:
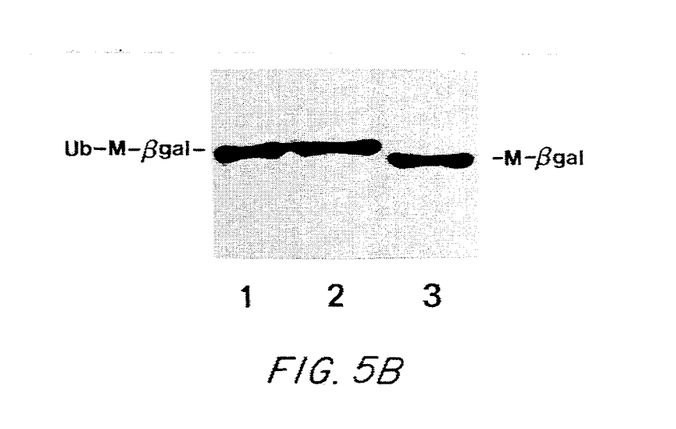

FIG. 5B shows a fluorograph of a 6% polyacrylamide-SDS gel demonstrating the ability of the UBP1 protease to deubiquitinate a ubiquitin-β-galactosidase fusion. Lane 1 contains [$^{35}$S]Ub-Met-βgal treated, in a mock reaction, with the buffer alone. Lane 2 contains the products of an otherwise identical reaction in which *E. coli* JM101 containing no plasmid was used as a source of extract (no deubiquitination is observed). Lane 3 contains the products of a reaction in which *E. coli* JM101 containing the plasmid pJT60 was used as a source of extract (note the ~8 kD decrease in molecular mass corresponding to the cleavage of the ubiquitin moiety off the ~115 kD Ub-M-βgal).

Figure 5C:
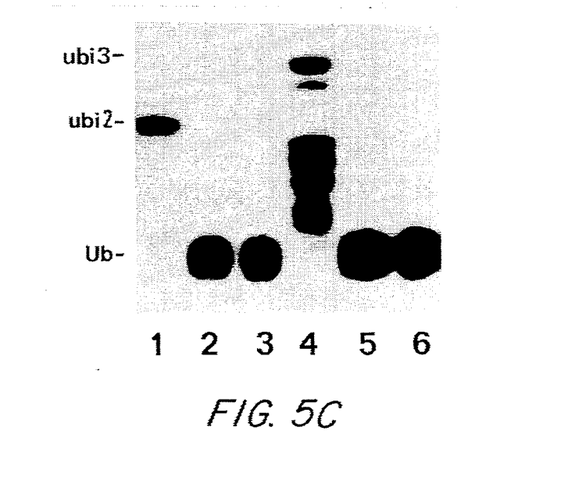

FIG. 5C represents a demonstration of in vitro deubiquitination of natural ubiquitin fusions to yeast ribosomal proteins (UBI2 and UBI3) by the yeast UBP1 protease. Lane 1 shows an extract from *E. coli* JM101 containing a plasmid that expressed UBI2, a natural ubiquitin-ribosomal protein fusion from *S. cerevisiae* that had been subjected to electrophoresis in a 12% polyacrylamide-SDS gel, blotted onto polyvinylidene difluoride membrane, and detected using a rabbit anti-ubiquitin antibody, with subsequent application of a secondary goat anti-rabbit antibody linked to alkaline phosphatase, and colorgenic substrates of alkaline phosphatase. Lane 2 and lane 1 represent identical samples except that the UBI2-containing extract was treated with extract from *E. coli* JM101 containing the UBP1-expressing plasmid pJT60. Lane 3 and lane 1 represent identical samples except that the UBI2-containing extract was treated with a whole cell yeast extract. Lane 4 and lane 1 represent identical samples except that an extract from *E. coli* JM101 contained a plasmid that expressed UBI3, another natural ubiquitin fusion (to a different yeast ribosomal protein). Lane 5 and lane 2 represent identical samples except that the yeast UBI3 protein was used as substrate for the UBP1 protease. Lane 6 and lane 3 represent identical samples except that the UBI3 protein as substrate. "ubi3," "ubi2," and "Ub" indicate the positions of the UBI3, UBI2 and free ubiquitin protein species. Bands in lane 4 that migrate faster than the UBI3 band are the products of a partial, nonspecific degradation of the yeast UBI3 protein in *E. coli* extract, with the proteolytic cleavages being confined to the non-ubiquitin portion of UBI3, since the entire sample of lane 4, when treated with the UBP1 protease, yields undegraded ubiquitin (lane 5).

EXAMPLE 2

Figure 6A:
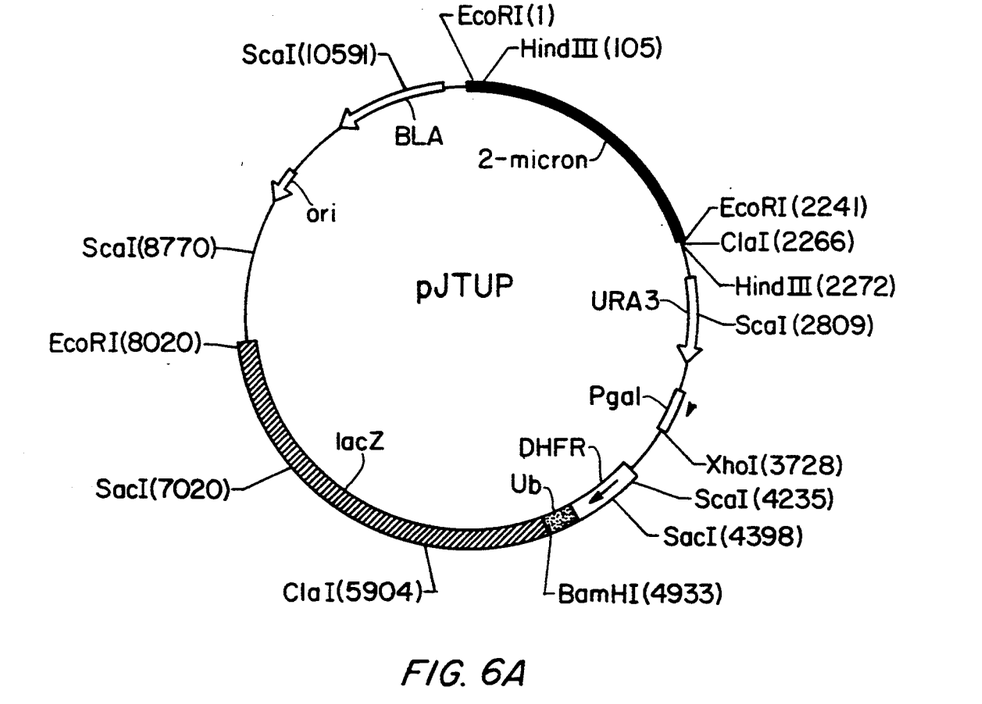

To determine whether a sandwich-type ubiquitin fusion protein in which the ubiquitin moiety had an amino-terminal extension was a substrate for UBP1, a plasmid was constructed that encoded a triple fusion protein consisting of an amino-terminal dihydrofolate reductase (DHFR) moiety, a flexible linker region of three glycine residues and a serine, followed by ubiquitin and Met-βgal moieties (FIG. 6A). The mouse DHFR gene was isolated on a BamHI/HindIII fragment from a plasmid encoding Ub-Met-DHFR (Bachmair and Varshavsky, Cell 56:1019–1032 (1989)). This fragment was treated with Klenow PolI to fill in the ends, and KpnI linkers were ligated. The fragment was then cut with KpnI to yield a 678 bp fragment which was cloned into the KpnI site in a modified Ub-Met-βgal expression vector in which the second codon of the ubiquitin moiety was altered to encode a KpnI site (Gonda et al., J. Biol. Chem. 264:16700–16712 (1989)). This procedure yielded a plasmid that encoded DHFR, ubiquitin (without the initial Met codon) and Met-βgal, with the open reading frames for each moiety not yet aligned into a single open reading frame. To effect the alignment of the open reading frames and to position the initiator codon of DHFR correctly with respect to the GAL promoter in the vector, site-directed mutagenesis was performed at two locations in the plasmid.

The plasmid was cut with BamHI and HindIII, and the ~2.76 kb fragment encoding DHFR, ubiquitin and the first few residues of Met-βgal was cloned into M13mp19 that had been cut with the same enzymes. Oligonucleotide-mediated, site-directed mutagenesis was performed using the single-stranded M13 derivative and standard protocols. The first oligodeoxynucleotide was designed to produce a 20 bp deletion that would bring the initiator codon of DHFR to a proper position relative to the GAL promoter of the vector. The second oligodeoxynucleotide was designed to bring together the reading frames of DHFR and ubiquitin, and to introduce the 4-residue spacer (-Gly-Gly-Gly-Ser-) between the DHFR and ubiquitin moieties. After mutagenesis, DNA clones were tested for incorporation of both changes by direct nucleotide sequencing using the chain termination method.

Double stranded, replicative form (RF) of the desired M13 clone was isolated and digested with BamHI and XhoI. The resulting ~1.2 kb fragment was cloned into the ~9.87 kb fragment of a Ub-Met-βgal expression vector digested with the same enzymes, replacing the Ub-Met-coding fragment with the DHFR-Ub-Met-coding fragment produced by the site-directed mutagenesis. This last step yielded an expression vector that encoded the triple fusion DHFR-Ub-Met-βgal. The vector was named pJTUP (FIG. 6).

pJTUP was used to test whether a ubiquitin fusion in which the ubiquitin moiety is located between two non-ubiquitin moieties would be a substrate for cleavage by UBP1. In E. coli metabolically labelled with [$^{35}$S]methionine, the fate of expressed DHFR-Ub-Met-βgal was determined in the presence or absence of UBP1 using immunoprecipitation with a monoclonal antibody to β-galactosidase, followed by polyacrylamide-SDS gel electrophoresis and fluorography (FIG. 6B).

Figure 6B:
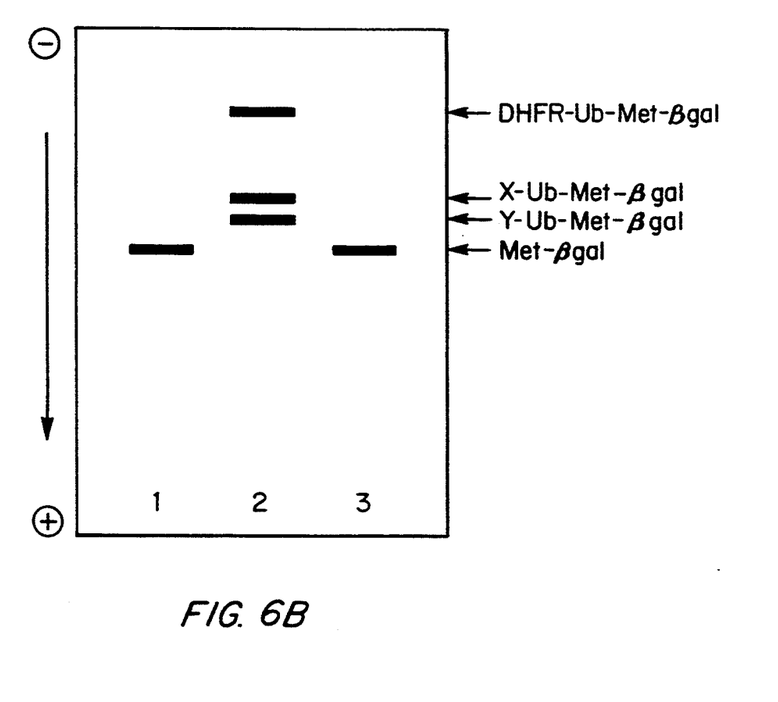

In FIG. 6B (a schematic representation of the results), lane 1 shows the fluorogram of an electrophoretically fractionated sample produced as follows: an aliquot of a stationary culture of E. coli carrying a plasmid expressing Ub-Met-βgal and a plasmid expressing UBP1, was diluted 1:100 into fresh Luria Broth. The culture was grown at 37° C. with vigorous shaking to an $A_{600}$ of 0.3. 1 ml of the culture was spun at 12,000×g for 1 minute. The supernatant was discarded and the pellet was resuspended in 50 μl of M9 medium supplemented with 0.2% glucose. The cells were incubated at 37° C. for 10 minutes and then 20 μCi of [$^{35}$S]methionine was added. Incubation was continued for 2 more minutes and unlabeled L-methionine was then added to a final concentration of 30 mM. The cells were then incubated for 5 minutes at 37° C., and subsequently lysed by the addition of 50 μl of lysis buffer (4% SDS, 125 mM Tris-HCl (pH 6.8)), followed immediately by heating at 100° C. for 4 minutes.

Immunoprecipitation using a monoclonal antibody to β-gal was then carried out. The lysate was diluted by the addition of 1 ml immunoprecipitation buffer (IP buffer) (1% Triton X-100, 0.5% Na-deoxycholate, 0.15M NaCl, 50 mM Tris-HCl (pH 7.5), 20 mM NaN$_3$, 5 mM EDTA, 1 mM phenylmethylsulfonyl fluoride). The sample was centrifuged at 12,000×g for 10 minutes at 4° C. The upper 0.9 ml of the supernatant was collected in a fresh tube to which 6 μl of a concentrated tissue culture supernatant containing a monoclonal antibody to βgal (Bachmair et al., Science 234:179–186 (1986)) was added. The tube was incubated on ice for 1 hour. 10 μl of a 50% suspension of Protein A linked to Sepharose beads (Repligen) was then added, and the tube was rotated slowly for 30 minutes at 4° C. The tube was then centrifuged for 15 seconds at 12,000×g, and the supernatant was discarded. The beads were washed 3 times at 4° C. with 1 ml of IP/SDS buffer (IP buffer plus 0.1% SDS (w/v)), with 15-second centrifugation at 12,000×g to precipitate the protein A-sepharose beads. The final pellet was resuspended in 15 μl of a 3-fold concentrated electrophoretic sample buffer (30% glycerol, 3% SDS (w/v), 15 mM EDTA, 0.2M 2-mercaptoethanol, 0.3 μg/ml bromophenol blue, 375 mM Tris-HCl, (pH 6.8)), and fractionated by polyacrylamide-SDS gel electrophoresis, followed by fluorography. A fluorogram of the gel (represented in lane 1 of FIG. 6B) revealed that the Ub-Met-βgal was cleaved at the ubiquitin-βgal junction by the simultaneously expressed UBP1 to yield the expected product, Met-βgal.

The sample represented in lane 2 was identical to that in lane 1 except that the triple fusion, DHFR-Ub-Met-βgal, was expressed in E. coli that lacked UBP1. Note that in addition to the full-length DHFR-Ub-Metβgal, this lane also contains bands representing shorter proteins. These are the result of either alternative initiation sites within the upstream (DHFR) moiety of the triple fusion, or nonspecific endoproteolytic cuts within that moiety. The smaller products are denoted by X- and Y-Ub-Met-βgal, respectively.

The sample represented in lane 3 was identical to that in lane 2 except that the triple fusion DHFR-Ub-Met-βgal was expressed in the presence of UBP1. Note that UBP1 efficiently cleaves all three triple fusion proteins (DHFR-Ub-Met-βgal, X-Ub-Met-βgal, and Y-Ub-Met-βgal) at the Ub-βgal junction, yielding Met-βgal.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An essentially pure ubiquitin-specific protease designated UBP1.

2. The essentially pure ubiquitin-specific protease of claim 1 having an amino acid sequence as shown in FIG. 4.

3. A method for cleaving ubiquitin from a fusion protein between ubiquitin and a non-ubiquitin protein or peptide, comprising contacting the fusion protein with a ubiquitin-specific protease designated UBP1.

4. The method of claim 3 wherein the ubiquitin-specific protease consists essentially of the amino acid sequence as shown in FIG. 4.

5. A method for cleaving ubiquitin from a sandwich fusion protein comprising a ubiquitin moiety fused between a first and a second non-ubiquitin moiety, the method comprising contacting the sandwich fusion protein with a ubiquitin-specific protease designated UBP1.

6. The method of claim 5 wherein the ubiquitin-specific protease consists essentially of the amino acid sequence as shown in FIG. 4.

7. The method of claim 6 wherein the first non-ubiquitin moiety is streptavidin.

* * * * *